United States Patent [19]

Kross et al.

[11] Patent Number: 4,891,216

[45] Date of Patent: Jan. 2, 1990

[54] DISINFECTING COMPOSITIONS AND METHODS THEREFOR

[75] Inventors: Robert D. Kross, Bellmore; Carol A. Zamojcin, Floral Park, both of N.Y.

[73] Assignee: Alcide Corporation, Norwalk, Conn.

[21] Appl. No.: 38,016

[22] Filed: Apr. 14, 1987

[51] Int. Cl.$^4$ .............. A61K 31/74; A61K 31/78; A01N 59/00

[52] U.S. Cl. ............................ 424/78; 424/81; 424/661

[58] Field of Search .................. 424/78, 661, 81

[56] References Cited

U.S. PATENT DOCUMENTS

| | | | |
|---|---|---|---|
| 2,071,091 | 2/1937 | Taylor | 424/661 |
| 2,095,092 | 10/1937 | Barton | 424/665 |
| 2,253,368 | 8/1941 | Dubeau | 252/187.23 |
| 2,255,694 | 9/1941 | Beale | 424/661 |
| 2,332,180 | 10/1943 | Soule | 252/187.23 |
| 2,701,781 | 2/1955 | de Guevara | 424/658 |
| 2,842,422 | 7/1958 | Mosse | 8/108.1 |
| 3,065,040 | 11/1962 | Waibel | 8/108.1 |
| 3,082,146 | 3/1963 | Wentworth et al. | 424/661 |
| 3,271,242 | 9/1966 | McNicholas et al. | 424/661 |
| 3,297,578 | 1/1967 | Crutchfield et al. | 252/541 |
| 3,386,915 | 6/1968 | Rutschi et al. | 424/661 |
| 3,843,548 | 10/1974 | James | 424/665 |
| 3,950,554 | 4/1976 | Prince | 424/665 |
| 4,035,483 | 7/1977 | Bunyan | 424/665 |
| 4,067,962 | 1/1978 | Juneja | 424/48 |
| 4,084,747 | 4/1978 | Alliger | 424/65 |
| 4,086,333 | 4/1978 | Bredwell | 424/431 |
| 4,104,190 | 8/1978 | Hartshorn | 424/663 |
| 4,128,631 | 12/1978 | Lundmark et al. | 424/78 |
| 4,296,102 | 10/1981 | Laso | 424/615 |
| 4,296,103 | 10/1981 | Laso | 424/615 |
| 4,303,546 | 12/1981 | Waegerle | 252/DIG. 11 |
| 4,317,814 | 3/1982 | Laso | 424/613 |
| 4,330,531 | 5/1982 | Alliger | 424/661 |
| 4,388,204 | 6/1983 | Dimond et al. | 252/98 |
| 4,410,442 | 10/1983 | Lucas et al. | 252/106 |
| 4,507,285 | 3/1985 | Kühne | 424/615 |
| 4,547,381 | 10/1985 | Mason et al. | 426/316 |
| 4,554,091 | 11/1985 | Jones et al. | 252/186.43 |
| 4,585,482 | 4/1986 | Tice et al. | 424/149 |
| 4,695,453 | 9/1987 | Tuominen et al. | 424/78 |

FOREIGN PATENT DOCUMENTS

| | | |
|---|---|---|
| 959238 | 12/1974 | Canada . |
| 965699 | 4/1975 | Canada . |
| 2329753 | 12/1973 | Fed. Rep. of Germany . |
| 2343171 | 3/1975 | Fed. Rep. of Germany . |
| 56116393 | 2/1983 | Japan . |
| WO85/0417 | 9/1985 | PCT Int'l Appl. .............. 424/149 |
| 496247 | 11/1938 | United Kingdom . |
| 880507 | 10/1961 | United Kingdom . |

OTHER PUBLICATIONS

Chemical Abstract 45873g, Mar. 4, 1968.
Balsan et al. eds., Chapter 15 in *Cosmetics Science and Technology,* Wiley Interscience, New York, Second Edition, *The Merck Index,* pp. 237, (1968).

*Primary Examiner*—Joseph L. Schofer
*Assistant Examiner*—Carmen Pili-Curtis
*Attorney, Agent, or Firm*—Seed and Berry

[57] ABSTRACT

There is disclosed, in one aspect, a composition for forming a protective barrier while disinfecting substrates such as human or animal skin. The composition comprises two gels adapted to be simultaneously applied and mixed in situ and to adhere onto the substrate. The first gel comprises an aqueous solution containing suitable amounts of a protic acid, preferably lactic acid. The second gel comprises an amount of a metal chlorite such as sodium chlorite, such that the chlorite ion concentration in the form of chlorous acid in the combined gels is no more than about 15% by weight of the total amount of chlorite ion concentration. The second gel also contains a polysulfonic acid salt. The anion of that salt has the formula:

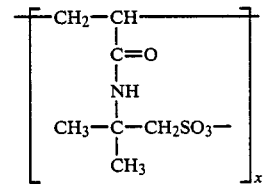

wherein X has a value such that the molecular weight of the anionic portion of the polymer is from about 1,000,000 to about 5,000,000. In another aspect, there is disclosed a method for treating skin diseases. This method comprises applying to the skin an effective amount of the above-noted composition.

14 Claims, No Drawings

DISINFECTING COMPOSITIONS AND METHODS THEREFOR

BACKGROUND OF THE INVENTION

This invention relates generally to compositions for disinfecting substrates as well as to processes for preparing and using such compositions.

The term "disinfectant" is used in this specification to broadly include any substance or composition that disinfects, sanitizes, deodorizes, sterilizes, or kills germs.

The use of chlorine compounds in various types of disinfectant compositions is well known. Chlorine compounds suggested for use in this regard include, for example, sodium hypochlorite, used in World War I as a wound irrigant, and chlorinated phenols, such as m-chlorophenol. These compounds have increased bactericidal activity and reduced toxicity, in some instances, when compared to non-chlorinated phenols. Thus, m-chlorophenol has a phenol coefficient of 5.9 (*S. aureus*) to 7.4 (*B. typhosus*). Other chlorine compounds having some form of disinfectant utility include, for example, chlorine gas itself, chlorine dioxide, chloramine T, calcium hypochlorite (a standard swimming pool disinfectant), chloropicrin (a larvicide), chloroform (a fumigant), chlordane (an insecticide), and chloromycetin (an antibiotic).

Chlorine dioxide in particular has been found to be an especially effective disinfectant. This compound is quite versatile and has long been used as a bleaching agent such as in the oxidizing of the natural colorant present in cotton, wood pulp and other cellulosic fibrous material. In such uses, chlorine dioxide, though performing an oxidizing function, is nevertheless non-injurious with respect to the fibrous material.

Particularly useful disinfecting compositions which employ chlorine containing compounds are disclosed in U.S. Pat. Nos. 4,330,531 and 4,585,482. These compositions comprise chlorite salts, such as sodium chlorite, in combination with weak organic acids, such as lactic acid, to provide particularly effective disinfectant compositions. These compositions are useful in topically treating skin diseases such as acne and in toothpastes.

One particularly prevalent disease is mastitis in dairy herds. Mastitis is a highly infectious disease which affects the bovine udder. The losses in dairy production resulting from this disease are staggering. For example, in the United States alone, these losses are estimated to be in the hundreds of millions of dollars. Mastitis not only reduces the production of higher yielding animals, but also shortens their productive life.

It is well known that mastitis is transmitted from animal to animal. It has also been established that the only route of transmission of the disease is through the teat orifice. Conditions which are held primarily responsible for the high incidence of mastitis include poor udder hygiene and physical damage to the teats. Dairymen and veterinarians have long sought a conditioning and protective composition which is economical and also provides facility of use. A composition which would improve the normal condition of the udder and teats and would also aid in preventing or effectively reducing the incidence of mastitis would serve to substantially increase both the production and productive life of a dairy herd.

Infectious mastitis is caused by microorganisms. Prior art treatments, such as the use of sulfanilimide, have been only partially effective in controlling the disease because such treatments are useful against only one type of microorganism which causes mastitis but are not useful against other types. Since the infection is usually of a mixed character, it follows that the effectiveness of drugs such as sulfanilimide is limited for all practical purposes.

It has also been suggested to use penicillin for the treatment of mastitis. The use of this compound is not desirable, however, in view of the high cost and extraordinary conditions necessary for the preservation and use of penicillin.

It has been proposed in U.S. Pat. No. 3,222,252 to treat mastitis with a preparation which comprises a blend of edible, semi-drying oils and drying oils together with a fatty acid ester, skin emollient, film forming agent. It is said that the presence of a drying oil in the preparation is essential to provide the desired film forming property. But for the most part, these film forming based treatments of mastitis have been unsuccessful. The use of iodine and peroxide in conjunction with latex emulsion films has led to other problems, including milk contamination and skin irritation.

The use of compositions comprising metal chlorite and a weak organic acid such as lactic acid, are disclosed in U.S. Pat. No. 4,330,531. A chlorine dioxide releasing compound offers to substantially alleviate the problems associated with the prevention of mastitis. For this application, the use of a gelling agent to generate a viscous topical gel is essential. The viscosity is needed for proper adhesion to the skin surface for an extended length of time.

Past attempts to create a useful viscous topical gel containing chlorine dioxide releasing compounds have been less than completely successful. Of the gelling agents tried, none combined the properties needed for substantial effectiveness. Carbohydrate based gels lose their viscosity at higher pH's as the alkaline chlorites break down the long polymer chains. Inorganic thickeners, such as bentonite clays, participate in the reaction between the acid and chlorite, and tend to form stringy, unsuitable gels.

The search has continued for a viscous topical gel composition capable of embodying alkaline chlorites for the treatment and prevention of skin disease, infection and irritation on humans and other animals. This invention was made as a result of that search.

OBJECTS AND SUMMARY OF THE INVENTION

Accordingly, it is a general object of the present invention to avoid or substantially alleviate the above-identified problems of the prior art.

Another object of the present invention is to provide a viscous topical gel composition for the improved treatment of skin infection and irritation on humans and animals.

A further object of the present invention is to provide a method for treating and preventing skin infections and irritations on humans and animals.

A more specific object of the present invention is to provide a viscous, disinfectant, topical gel composition which will form a long lasting solid shield on cow teats for the prevention and treatment of mastitis.

Other objects and advantages of the present invention will become apparent from the following summary of the invention and description of its preferred embodiments.

The present invention provides, in one aspect, a composition for disinfecting substrates. This composition comprises two gels adapted to be mixed and applied so as to adhere onto the substrate. The first gel contains an aqueous solution containing suitable amounts of a protic acid. The second gel contains an amount of metal chlorite such that, when combined in equal parts with the first gel, the chlorite ion concentration in the form of chlorous acid is no more than about 15% by weight of the total amount of chlorite ion concentration. The second gel also contains a polysulfonic acid salt wherein the anion of the salt has the formula:

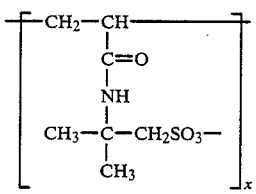

wherein X has a value such that the molecular weight of the anionic portion of the polymer is from about 1,000,000 to about 5,000,000.

In another aspect, the present invention provides a method for treating skin diseases. The method comprises applying to the affected area of the skin an effective amount of the above-identified composition.

DETAILED DESCRIPTION OF THE INVENTION

The composition of this invention is formed by combining one gel which comprises a dilute aqueous solution of metal chlorite with another gel which comprises a dilute aqueous solution containing a weak organic acid. The gel containing the metal chlorite also contains the polysulfonic acid salt. The concentrations of chlorite and acid are relatively low.

This composition provides a metastable chlorous acid composition formed from relatively small amounts of chlorite and acid. This composition is capable of generating chlorine dioxide over a long period of time at continuing levels of effectiveness. As chlorine dioxide forms, more of the chlorite converts to chlorous acid by interacting with hydrogen ions further generated by ionization of the organic acid.

Weak organic acids which may be used in the present invention include citric, malic, tartaric, glycolic, mandelic or other structurally similar acids as described in Formula I hereinbelow.

FORMULA I

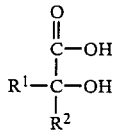

$R^1$ and $R^2$ may be the same or different and may be selected from the group consisting of hydrogen, methyl, —$CH_2COOH$, —$CH_2OH$, —$CHOHCOOH$, and —$CH_2C_6H_5$. The pK of the organic acid is from about 2.8 to about 4.2, preferably from about 3.0 to about 4.0.

Compositions of a metal chlorite and the weak organic acids of Formula I are disclosed in copending U.S. patent application Ser. No. 850,009, which was filed on Apr. 10, 1986. The entire disclosure of that application is hereby incorporated by reference.

The gel containing the protic acid also contains a gelling agent or thickener which is well known to those skilled in this art. Any gelling agent or thickener which is non-toxic and non-reactive with the other ingredients of the composition may be used, such as cellulose, gels, typically methyl cellulose or preferably, hydroxy ethyl cellulose. Furthermore, that gel may also contain a preservative, such as benzyl alcohol or sodium benzoate. Other additives, such as buffers to adjust the pH of the composition to become more compatible with the skin, may be used.

The amount of thickener in the protic acid-containing gel may be generally from about 0.5% to about 5, typically from about 0.8 to about 4%, and preferably from about 1 to about 3 percent of the gel, by weight, of the total composition. The amount of preservative in the gel may be generally from about 0.01 to about 0.05%, typically from about 0.01 to about 0.04%, and preferably from about 0.02 to about 0.03 percent, by weight, of the total composition.

The chlorine dioxide liberating compound or metal chlorite and the protic acid are present in separate gels, and the amount of the preservative is present in only that gel containing the protic acid. Approximately equal amounts of the separate gels should be used.

The gel containing metal chlorite is thickened with a polysulfonic acid salt. The amount of polysulfonic acid salt added will depend on the desired use of the resulting composition. For a topical cream, toothpaste or topical gel for the treatment of facial acne, the amount of thickener in the metal chlorite containing gel may be generally from about 5% to about 15%, typically from about 5% to about 10%, and preferably from about 6 to about 8%, by weight, polysulfonic acid salt based upon the total composition. For a composition particularly suited to be used as a teat dip for treating cow udders, the amount of thickener in the metal chlorite containing gel may be generally from about 0.5 to about 5%, typically from about 1 to about 4%, and preferably from about 2 to about 3%, by weight, solid polysulfonic acid salt based upon the total composition.

These polysulfonic acid salts are polymers of 2-acrylamido-2-methylpropane sulfonate. The preparation of such polymers is described in U.S. Pat. No. 4,128,631, Canadian Pat. No. 864,433 and in German OLS No. 2,153,292 laid open May 4, 1972, all of which ae herein incorporated by reference.

The pH of the gel containing the polysulfonic acid salt is generally greater than about 8, typically from about 9 to about 12, and preferably from about 10 to about 11.5.

The polymers useful in the present invention are prepared from

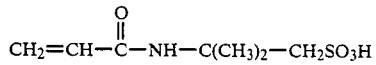

or a salt thereof. The polymerization reaction may be accomplished by solution, emulsion or suspension polymerization processes. The medium for the polymerization is conveniently water, an alcohol, or a mixture thereof. The choice of the medium is best dictated by the requirements of the final composition to be formulated.

The polymerization reaction is temperature, pH, and catalyst sensitive. In addition, it is desirable to exclude oxygen from the reaction vessel used to form the polymer, as that material inhibits the polymerization process. The catalysts which are included to enhance the rate of polymerization are materials such as ammonium bisulfite, ferrous sulfate, hydrogen peroxide, sodium metabisulfite, or other redox catalysts.

The polymer may be varied in molecular weight by controlling the amount of the catalyst, the pH, or the rate of addition of the monomer to the reaction vessel. The polymerization may be facilitated by converting the monomer from its acid form to a salt which is water-soluble.

The salts of the polymer preferably contain as cations, sodium, potassium, ammonium, monoethanolamine, diethanolamine, triethanolamine, and 2-amino-2-methyl-1-propanol as well as mixtures thereof. The foregoing list is merely exemplary of water-soluble salts which may be used. Also within the scope of the present invention are water-insoluble salts wherein the final composition is not adversely affected by precipitation of the polymer. Such products where water-insoluble salts of the polymer may be utilized are toothpastes, or substantially non-aqueous products such as topical creams. Examples of suitable water-insoluble salts are those of calcium and magnesium.

As was previously mentioned, the molecular weight of the polymer may be controlled by the pH, the rate of addition of the monomer, or the judicious use of the catalyst. It has been found desirable to utilize the afore-described polymers having a molecular weight of from about 1,000,000 to about 5,000,000, more preferably from about 2,500,000 to about 4,500,000, to improve the viscosity and film forming characteristics of the composition. That is, extremely high molecular weight polymers of the type described may result in a pituitive or stringy consistency of the end product. It has therefore been found desirable to limit the pituitiveness by selecting the preferred molecular weight range. To this end, any common chain transfer agent, such as mercaptosuccinic acid, may be used to limit the molecular weight of the polymer.

It is noted that the terminal groups on the polymer have little bearing on the desired properties of the final composition and are thus not specified. The terminal groups are most often hydrogen, but may also be hydroxyl, sulfate, sulfonate or

All alcohols, particularly the monohydric alcohols, may be used as ingredients with the polymer. Alcohols ($C_1$–$C_{24}$) which are non-irritating to the skin, such as methanol, ethanol, isopropanol, propyl, lauryl, myristyl, cetyl, and stearyl, as well as mixtures thereof, are preferred. Polyols such as glycerine, or ethylene glycol or propylene glycol may be utilized advantageously with the polymer. The choice of the alcohol to be utilized with the particular polymer of the composition of the present invention will ordinarily be dictated by product aesthetics and physical form of the composition. For instance, when liquid compositions are desired, the lower alcohols are preferably utilized, while cream compositions within the scope of the present invention will normally require the higher alcohols. Where the compositions of the present invention contain ingredients other than the polymer or the alcohol in substantial amounts, the choice of the particular alcohol becomes less important.

A desirable variable of the present invention is the incorporation of water with the polymer. A resultant increase in viscosity of the water is noted with no adverse effects on the stability of the product, that is, water is a highly suitable carrier which may be used as a vehicle for contacting the polymer and the substrate. The particular weight ratios at which the desirable increase in viscosity occurs for mixtures of the polymer and water are respectively from about 1:10,000 to about 1:100. Preferably this ratio is in the range of from about 1:1000 to about 1:500. Within the aforementioned range, highly viscous compositions are obtained with low solids content. Such compositions are desirable in that they allow compositions such as topical creams or gels, acne gels, or teat dips to be formulated in a thickened state, providing greater ease of application.

The gel containing the protic acid and the gel containing the metal chlorite are mixed either before application to the affected substrate or preferably in situ. After the gels are mixed, the pH of the final composition is generally less than about 7, typically from about 2 to about 5, and preferably from about 2.5 to about 4.

In the present invention, the composition is ordinarily used at a level of about 0.001 gram per square centimeter to about 0.1 gram per square centimeter of the affected substrate.

The present invention is illustrated by the following examples. Unless otherwise noted, all parts and percentages in the examples as well as the specification and claims are by weight.

EXAMPLE I

This Example illustrates the preparation of a toothpaste composition according to the present invention.

There is prepared a two-part disinfectant toothpaste composition according to the invention having a first base paste or gel and a second activator paste or gel.

The formulations of the two toothpaste parts on a percent weight to weight basis are as follows:

| TOOTHPASTE | |
|---|---|
| BASE | % W/W |
| Poly (sulfonic Acid) [16% aqueous solids] | 45.0 |
| Sodium hydroxide, 1N | 40.0 |
| Bentonite | 2.0 |
| Sodium lauryl sulfate | 1.0 |
| Titanium dioxide | 1.0 |
| Silica, amorphous | 0.5 |
| Sodium chlorite | 1.0 |
| Water | q.s. |
| ACTIVATOR | |
| Glycerin | 10.0 |
| Magnesium aluminum silicate | 5.0 |
| Hydroxyethylcellulose | 2.0 |
| Malic acid | 1.5 |
| Flavor, wintergreen | 0.4 |
| FD & C Blue #1 (0.5% soln) | 0.06 |
| Sodium benzoate | 0.05 |
| Sodium saccharine | 0.05 |
| Water | q.s |

The pH of the composition resulting from the mixture of substantially equal portions of the base and activator gels of the above formulation is about 4.15.

The base gel and the activator gel are preferably stored separately prior to use, e.g., in a double compartment tube. The two gels are mixed, preferably just prior to use, in substantially equal amounts and the mixture is used in the normal manner as a toothpaste. Alternatively, substantially equal portions of the gels are placed in the mouth and mixed by the brushing action while the subject brushes his or her teeth.

EXAMPLE II

This Example illustrates the use of the present invention as a teat dip for application to cow udders.

A first gel is prepared by mixing the following ingredients:

| | |
|---|---|
| Rheothik 80-11 poly (sulfonic acid) [16% aqueous solids] | 16.00% |
| NaOH, 1N | 16.00% |
| Nacconol 90F (Sodium dodecylbenzene sulfonate) | 1.80% |
| Sodium chlorite | 0.64% |
| EDTA, Na$_4$ | 0.19% |
| Hi-Sil T-600 (Silica) | 2.50% |
| Water | q.s. |

A second gel is prepared by mixing the following ingredients:

| | |
|---|---|
| Lactic Acid | 2.64% |
| Natrosol 250MR | 1.00% |
| Isopropyl alcohol | 2.00% |
| Sodium Benzoate | 0.04% |
| Poloxamer 188 | 0.40% |
| FD&C Yellow #5 | 0.30% |
| Water | q.s. |

The two solutions are blended, preferably just prior to application. The resulting gel is applied to the cow teat, forming a solid shield around the teat. The film thus formed, following drying, provides a long lasting and continuously acting disinfectant in direct contact with the skin surface.

EXAMPLE III

This Example illustrates the preparation of a topical gel useful for the treatment of infection based facial acne.

A first gel is prepared by mixing the following ingredients:

| | |
|---|---|
| Rheothik 80-11 poly (sulfonic acid) [16% aqueous solids] | 45.0% |
| NaOH, 1N | 38.0% |
| Nacconol 90F | 1.8% |
| Na$_4$EDTA | 0.19% |
| NAClO$_2$ | 0.32% |
| Deionzed water | q.s. |

A second gel is prepared by mixing the following ingredients:

| | |
|---|---|
| Salicylic Acid | 2.0% |
| Isopropyl Alcohol | 30.0% |
| Sodium Benzoate | 0.04% |
| Natrosol 250MR | 2.1% |
| Pluronic F-68 | 0.4% |
| Deionzed water | 65.46% |

The first and second solutions are mixed, preferably just prior to use. The resulting gel is applied to the affected region of the skin. A film forms, creating a long lasting cover that provides a continuous supply of disinfectant to the covered area of skin for a prolonged period of time.

COMPARATIVE EXAMPLE

This Example illustrates the properties of compositions employing hydroxyethyl cellulose as a gelling agent for sodium chlorite in the preparation of a final composition comprising sodium chlorite and lactic acid.

Example I is repeated, but hydroxyethyl cellulose is used at the 2% level in place of the polysulfonic acid salt and excluding the same hydroxide. This gel is not storage stable for a commercially acceptable period of time. The cellulose gelling agent depolymerizes and loses viscosity.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A composition for disinfecting substrates and for forming a protective barrier comprising two gels adapted to be mixed and applied so as to adhere onto said substrate, said first gel comprising an aqueous solution containing suitable amounts of a protic acid, and said second gel comprising an aqueous solution of a metal chlorite such that, when the gels are combined, the chlorite ion concentration in the form of chlorous acid is no more than about 15% by weight of the total amount of chlorite ion concentration and wherein said second gel also contains a polysulfonic acid salt wherein the anion of said salt has the formula:

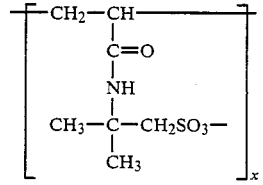

wherein X has a value such that the molecular weight of the anionic portion of the polymer is no greater than about 5,000,000, with the proviso that the composition contain from about 2.5% to about 7.5%, by weight, polysulfonic acid salt.

2. The composition of claim 1 wherein said protic acid has a pK of from about 2.8 to about 4.2.

3. The composition of claim 2 wherein said protic acid is salicylic acid.

4. The composition of claim 2 wherein said composition contains sufficient amounts of fillers and binders to form a topical cream.

5. The composition of claim 2 wherein said composition comprises sufficient amounts and kinds of fillers and binders to form a toothpaste.

6. The composition of claim 1 wherein said first gel comprises hydroxyethyl cellulose.

7. The composition of claim 1 wherein the molecular weight of the anionic portion of said polymer is from about 2,500,000 to about 4,500,000.

8. The composition of claim 1 wherein the cation of the polymer is selected from the group consisting of sodium, potassium, ammonium, monoethanolamine, diethanolamine, triethanolamine, and 2-amino-2-methyl-1-propanol and mixtures thereof.

9. A method for treating skin diseases comprising applying to the affected area of the skin an effective amount of a composition comprising two gels adapted to be simultaneously applied and mixed in situ and to adhere onto said substrate, said first gel comprising an aqueous solution containing suitable amounts of a protic acid, and said second gel comprising an aqueous solution of metal chlorite such that when the gels are combined, the chlorite ion concentration in the form of chlorous acid is no more than about 15% by weight of the total amount of chlorite ion concentration and wherein said second gel also contains a polysulfonic acid salt wherein the anion of said salt has the formula:

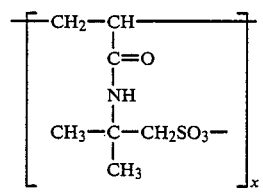

wherein X has a value such that the molecular weight of the anionic portion of the polymer is no greater than about 5,000,000, with the proviso that the composition contain from about 2.5% to about 7.5%, by weight, polysulfonic acid salt.

10. The method of claim 9 wherein said protic acid has a pK of from about 2.8 to about 4.2.

11. The method of claim 10 wherein said protic acid is salicylic acid.

12. The method of claim 9 wherein said first gel comprises hydroxyethyl cellulose.

13. The method of claim 9 wherein the molecular weight of the anionic portion of said polymer is from about 2,500,000 to about 4,500,000.

14. The method of claim 9 wherein the cation of the polymer is selected from the group consisting of sodium, potassium, ammonium, monoethanolamine, diethanolamine, triethanolamine, and 2-amino-2-methyl-1-propanol and mixtures thereof.

* * * * *